(12) United States Patent
Lo

(10) Patent No.: US 10,569,436 B2
(45) Date of Patent: Feb. 25, 2020

(54) DEVICE FOR CUTTING HAIR

(76) Inventor: Insa Lo, Steinenbronn (DE)

(*) Notice: Subject to any disclaimer, the term of this patent is extended or adjusted under 35 U.S.C. 154(b) by 606 days.

(21) Appl. No.: 13/877,168

(22) PCT Filed: Sep. 29, 2011

(86) PCT No.: PCT/EP2011/067030
§ 371 (c)(1),
(2), (4) Date: Jun. 19, 2013

(87) PCT Pub. No.: WO2012/041982
PCT Pub. Date: Apr. 5, 2012

(65) Prior Publication Data
US 2013/0340582 A1    Dec. 26, 2013

(30) Foreign Application Priority Data

Oct. 1, 2010    (DE) .................. 10 2010 041 881

(51) Int. Cl.
*B26D 1/08* (2006.01)
*B26D 1/04* (2006.01)
*B26D 7/01* (2006.01)

(52) U.S. Cl.
CPC .............. *B26D 1/04* (2013.01); *B26D 7/01* (2013.01); *Y10T 83/0405* (2015.04); *Y10T 83/748* (2015.04)

(58) Field of Classification Search
CPC .... B26D 1/08; A61B 10/1096; A61B 10/0009
USPC ............... 30/29.5; 600/654; 436/172; 83/13
See application file for complete search history.

(56) References Cited

U.S. PATENT DOCUMENTS

| 1,424,472 | A |   | 8/1922  | Goldberg |
| 2,843,135 | A | * | 7/1958  | Lisiewski ............... A24F 13/26 131/255 |
| 3,640,267 | A | * | 2/1972  | Hurtig et al. ................. 600/578 |
| 4,709,610 | A | * | 12/1987 | Pool ..................... B23D 45/042 83/229 |

(Continued)

FOREIGN PATENT DOCUMENTS

JP    2008 062370    3/2008

OTHER PUBLICATIONS

Stone et al. "Production of hair intercomparison materials for use in population monitoring programmes for mercury and methylmercury exposure" Fresnius' Journal of Analytical Chemistry, Bd. 152, Jan. 1, 1995, pp. 184-187.

*Primary Examiner* — Andrea L Wellington
*Assistant Examiner* — Fernando A Ayala
(74) *Attorney, Agent, or Firm* — Timothy M. Brown

(57) ABSTRACT

The present invention relates to a device to cut hair, fibers, or thin, flexible materials, comprising at least one retaining element (2) with a cylindrically formed interior that is suitable for immobilizing and potentially bundling in lengthwise direction a sample (1) to be cut, composed of a multiplicity of hairs, fibers, or thin, flexible materials, and a cutting device (3) that is suitable for cutting the sample that is immobilized and possibly bundled in lengthwise direction, in a direction that is substantially perpendicular to the cylinder axis of the interior of the retaining element (2). The present invention relates furthermore to a method making use of the device, as well as a hair section that can be produced with the device or the method.

9 Claims, 5 Drawing Sheets

(56) References Cited

U.S. PATENT DOCUMENTS

| | | | | |
|---|---|---|---|---|
| 4,872,384 A | * | 10/1989 | Borzym | B23D 21/00 83/319 |
| 5,033,344 A | * | 7/1991 | Ohneda | B21D 43/003 83/262 |
| 5,927,172 A | * | 7/1999 | Wang | B23D 23/00 83/454 |
| 6,049,984 A | * | 4/2000 | McGehee | A24F 13/24 131/248 |
| 7,748,305 B2 | * | 7/2010 | Strenio | B26D 3/08 83/861 |
| 2005/0201904 A1 | * | 9/2005 | Stripling | B01L 3/508 422/400 |
| 2005/0258285 A1 | * | 11/2005 | McCambridge et al. | 241/2 |
| 2008/0219885 A1 | * | 9/2008 | Horstman | A61B 10/0096 422/400 |
| 2009/0113719 A1 | * | 5/2009 | Smith | 30/113 |
| 2012/0311867 A1 | * | 12/2012 | Baker et al. | 30/92 |
| 2014/0031839 A1 | * | 1/2014 | Umar et al. | 606/133 |

* cited by examiner

DEVICE FOR CUTTING HAIR

TECHNICAL FIELD

The present invention relates to a device to cut hair, fibers, or thin, flexible materials, comprising at least one retaining element (2) with a cylindrically formed interior that is suitable for immobilizing and potentially bundling in lengthwise direction a sample (1) to be cut, composed of a multiplicity of hairs, fibers, or thin, flexible materials, and a cutting device (3) that is suitable for cutting the sample that is immobilized and possibly bundled in lengthwise direction, in a direction that is substantially perpendicular to the cylinder axis of the interior of the retaining element (2). The present invention relates furthermore to a process making use of the device, as well as a hair segment that can be produced with the device or the process.

DESCRIPTION

Because of its minimally invasive nature, hair analysis is of growing importance, for example in forensics, in the connection with examinations of substance abuse (for example, detection of common drugs such as cannabinoids, amphetamines, and benzodiazepine, detection of ethyl glucuronide for alcohol abuse), work-related medical examinations (for example, verification of exposure to contaminants), or in veterinary and sport-related medical fields (for example, to detect prohibited pharmacological materials). Detection of a wide variety of different materials in hair (such as narcotics, medications, and contaminants, for example) is possible because of the deposition of corresponding materials in the hair structure. These materials are initially transported by the blood and extend via the hair follicle into the growing hair, which preserves the substance for a long period of time.

Measurements normally form the basis of most examinations, analyses, and quantitative comparisons. In almost all cases, what cannot be measured cannot be improved. Measurements are not possible without standards. The vast majority of standards are reference materials. The reliability and veracity of measurements depends largely on the availability of reference materials. This is especially true for chemical measurements. For this reason, reference materials play a central role in the verification structures for chemical analysis.

Reference materials for liquid compounds such as whole blood, plasma, serum, or urine have become commercially established for forensic, toxicological, and clinical chemistry, whereas sufficiently standardized suitable reference materials for the solid matrix in hair are hardly available on the market. The primary reason for this is that such samples have not yet been able to be produced cost-effectively and in sufficiently large quantities.

A fundamental problem for the production of reference hair materials is to achieve sufficient homogeneity in large batches. In order to obtain commercially exploitable batches of at least 100 to 1000 grams, individual hair samples from multiple hair donors must be analyzed for suitability and combined into significantly larger batches. The homogeneity that can be achieved by combining such mixtures of solids depends largely on the number of particles and their size distribution, so that the aim shall be the smallest possible particle size. This must be correspondingly finer depending on how unfavorable the ratio is between the smallest individual sample to the total size of the batch, so as to provide a high statistical probability of a sufficiently uniform distribution. For this reason, the reduction in particle size of hair samples represents a decisive aspect for the production of larger batches of hair.

Each size reduction by means of cutting results in a mixture of particles of various size distributions, which previously could be controlled in only a very limited fashion. Mixtures of solid materials exhibit a size-dependent migration behavior in their particles, which only in the finest grindings (powder) ceases to play a role. This "popcorn effect" is correspondingly stronger, the greater the particles differ in their sizes. This leads to a gradual enrichment of smaller particles in the lower portion and larger particles in the upper portion of the mixture. A loss in homogeneity through separation processes is to be expected, especially during refilling processes (measurement, portioning) as well as following extended transport and storage periods for individually filled containers. However, a prerequisite for a reference material is that each individual sample is representative of the compound in the original entire batch.

Pulverization of hair by grinding is up to now the most suitable method for the production of large and at the same time homogeneous batches of hair. Various grinding devices and procedures are used: a dramatic increase in the number of particles can be achieved with all of them. However, pulverization involves several disadvantages: the mechanical destruction of the structural integrity of the hair fiber and extreme surface area increase achieved by grinding permit only limited comparability of ground hair reference samples with the specimens cut for analysis in pre-analytical washing and extraction steps. Thermal damage of the ground material potentially resulting from the grinding process has additional effects upon comparability. Since the terms required by forensic examinations demand that the specimens to be studied must be examined in cut condition, the powdered ground material is no longer suitable for monitoring the overall analytic procedure.

The European patent EP 1933985 B1 discloses a ball mill, suitable for quick, batch-wise reduction of medium-hard to hard samples to the finest particle sizes. These smallest particle sizes lead indeed to the desired homogenization, and thus avoid the "popcorn effect", but as a reference material they have the disadvantage of only minimal comparability, as a result of the of the structural differences from authentic cut specimens. The problem of thermal damage potentially occurring during the course of the milling process can be avoided by freezing the samples (c.f.: Spex Freezer/Mill). However, the disadvantages resulting from the structural differences between the reference and test materials mentioned above remain in force.

Granulation by cutting the extraordinarily delicate and difficult to handle hair fibers was previously only achievable manually, only for smaller amounts, and only with large variances in cut lengths of the hair particles so obtained. For example, there are devices to cut hair fibers within the prior art, which are generally composed of a retaining and a cutting device. Microtomes are a typical example of this group, which are suitable to cut individual hairs; however, they cannot be used to quickly and simply manufacture reference materials with sufficient homogeneity and defined size distribution, for example. In addition, this procedure comprises the disadvantage, that the material to be cut must be embedded; wherein paraffin, polyethylene glycol, celloidin, gelatin, agar, and synthetic resins are typically used. After cutting, this medium must be removed by one or more additional cleansing steps, whereby the risk of contaminating the hair with residues from the embedding medium is increased.

ILLUSTRATION OF THE INVENTION, ITS PURPOSE, THE SOLUTION, AND ADVANTAGES

Based on the aforementioned procedure of prior art, the present invention has the purpose of providing a device or procedure with which human or animal hair, fibers, and other long, flexible materials, can be prepared tightly bundled into segments of defined length with a controllable distribution of sizes, free from contamination, and while maintaining their structural integrity, which thus does not exhibit the abovementioned disadvantages of the prior art. The device or the procedure should function cost effectively and be well suited for routine use and especially for the production of reference materials. The segments produced by the device and the procedure should also exhibit excellent homogeneity.

This purpose underlying the invention is fulfilled by the devices or procedures defined in the claims, such as is apparent from the accompanying examples and experimental data.

In an initial aspect the present invention therefore relates to a device to cut hair, fibers, or thin, flexible materials. The device comprises at least one retaining element (2) with a cylindrically formed interior. The retaining element (2) is suitable here for immobilizing and potentially bundling in lengthwise direction a sample (1) to be cut, composed of a multiplicity of hairs, fibers, or thin, flexible materials. The device comprises in addition a cutting device (3). This cutting device (3) is suitable for cutting the sample that is immobilized and possibly bundled in lengthwise direction, in a direction that is substantially perpendicular (i.e., orthogonal) to the cylinder axis of the interior of the retaining element (2).

Experience has shown that any retaining element that comprises a cylindrically formed interior that is suitable to receive a sample to be cut of a multiplicity of hairs, fibers, or thin flexible materials, can be used as the retaining element. According to the invention, the interior is cylindrically formed, meaning that the interior is enclosed by a base and an upper surface, as well as by an encasing or cylindrical surface that is formed by parallel lines. It is preferably a straight cylinder. In a preferred embodiment, the cylindrically formed retaining element has at least one open end. The retaining element may be composed of any freely selected material that makes immobilizing and potentially bundling the sample possible. According to the invention, immobilizing is understood to be slip-free storage of the sample within the cylindrically formed interior, wherein a dislocation of either the entire sample with respect to the retaining element, as well as of individual sample components with respect to each other shall be prevented, both prior to and during the cutting procedure. Bundling of the sample designates the alignment of the sample parallel to the axis of the cylindrically formed interior of the retaining element and/or the to a large extent spatially tight arrangement of the components of the sample to one another. The absence of dislocations due to immobilization and potentially due to bundling is of particular advantage for the homogeneity of the segments resulting from the cutting process, since the thus immobilized and possibly bundled sample exhibits overall a more homogeneous character than non-bundled cut material, due to the high volume proportion of the sample and minimal formation of cavities. In addition, a tight bundling can largely prevent pulling out individual fibers from the sample during the cutting procedure.

The retaining element is itself preferably cylindrically formed. For example, the retaining element can be a tube or a hollow cylinder with a likewise cylindrically formed interior. With regard to the geometry of the cylindrically formed retaining element, or its cylindrically formed interior, the base and upper surface as well as the thereby corresponding encasing surface may in principle be formed in a variety of possible shapes; the straight cylinder is preferably formed circular in cross-section, whereby a circular cylindrical shape with a right-angled vertical profile is obtained. The circularity of the base and upper surface of the retaining element or of the cylindrically formed interior has the particular advantage of being able to provide a largely uniform distribution of the inserted sample material in the interior. The cylindrically formed interior preferably has a diameter of 1 to 5 mm, preferably 2 to 4 mm, and in particular approximately 3 mm In this manner, for example 200 to 800, in particular 375 to 560 individual hairs lying alongside one another, with an average length density of 1 mg/15 cm, can be simultaneously immobilized and potentially bundled in the interior.

The retaining element is in principle not limited with regard to its length; here the extent of its length is preferably adjusted to the physical characteristics of the sample to be cut. The retaining element is advantageously formed in the shape of a pipe. A pipe is understood to be an elongated hollow body, whose length is generally much longer than its cross-section. In a particular embodiment, the retaining element is a tube, if the retaining member is substantially constructed of flexible material. Preferably, the retaining element comprises a length of 5 to 10 cm, in particular approximately 8 cm.

The material in the retaining element is in principle not subject to any particular restrictions. The sample is preferably cut off either directly above the retaining element or the retaining element is included with the cut portion. The material in the retaining element is in particular adjusted to the characteristics of the sample. The retaining element is preferably composed of a sliceable material. Ideally, the retaining element is composed substantially of a material that is selected from: organic or inorganic polymers, metal, paper, wound tubing, or combinations thereof. A polymer is understood to be any polymer or copolymer, which may also contain one or more common additives. The retaining element preferably consists of a polymer that is selected from the group of thermoplastic or elastomeric polymers, or a combination thereof, in particular from the thermoplastic polymers. For example, the retaining element can be a thermoplastic polymer tube. This is characterized by particularly advantageous material properties, since it is flexible over a wide temperature range, as well as high mechanical resistance, in particular, high resistances against wear, creasing, and tearing. Preferably, the retaining element possesses elastic characteristics, while simultaneously exhibiting sufficient firmness to retain a sample. Because of its strength, such a retaining element is superbly capable of immobilizing the sample material according to the invention, and potentially to bundle it to the required tightness. The retaining element consists preferably of a polymer that is selected from polystyrene, polyvinyl chloride, polyurethane, polyamide, polyethylene, polypropylene, or silicone, in particular of polyurethane.

With regard to the electrostatic charges that may be generated during the cutting procedure by frictional processes, and which may make the separation of the sample and retaining element more difficult after cutting, a retaining element composed of a polymer with a minimum possible surface resistance and/or minimal leakage resistance is preferred. The surface resistance is understood to be the electrical resistance that is measured on the surface of an object under defined conditions. Polymer surfaces may be electrostatically charged starting at a surface resistance of $10^{10}\square$. An object shall be designated as conductive when the surface resistance amounts to between approximately $10^4\square$ and $10^{11}\square$, measured at 23° C. and 30% relative humidity, or between circa $10^4\square$ and $10^9\square$, measured at 23° C. and 50% relative humidity. The retaining element according to the invention is preferably composed of a polymer with a surface resistance of at most $10^{10}\square$ in particular at most $10^8\square\square\square$ If the retaining element is composed of paper or of a polymer, then is it preferable when it is coated with a antistatic-acting layer over all or at least over part of its surface. The electric charge will thus be reduced during cutting. For example, the surface of the retaining element may entirely or partially coated with a layer of a conducting antistatic-agent (for example, vapor-deposited metal, such as for example copper, gold, or silver) or non-conducting antistatic-agent (for example, an application of quaternary ammonium salt, such as for example a polyquaternium, behentrimonium chloride, or cocamidopropyl betaine, an application of an aliphatic, optionally an ethoxyliated amine or amide, a phosphoric acid ester, a polyethylene glycol ester, or a polyol). Alternatively or in addition, the retaining element may also exhibit an intrinsic conductivity. Such a retaining element may be particularly advantageously used in the device according to the invention, since it does not present a contamination source for the sample. Here the observed loss in antistatic effect generated by frictional wear in the device according to the invention (for intrinsic antistatic agents as well) can be ignored, since the individual retaining elements formed of polymer are not repeatedly used after to the cutting procedure. For example, the retaining element may be composed of a polymer, such as for example polyurethane, in which a quaternary ammonium salt, such as for example a polyquaternium, behentrimonium chloride, or cocamidopropyl betaine, an aliphatic, optionally an ethoxyliated amine or amide, a phosphoric acid ester, a polyethylene glycol ester, or a polyol is intrinsically contained. It is especially advantageous when the retaining element is composed of a transparent or translucent polymer, in which indium tin oxide is embedded as an intrinsic antistatic agent. Indium tin oxide offers the advantage, that it is itself transparent, so that the sample can be seen within the retaining element from outside.

In an alternative embodiment, the retaining element may be constructed from a conductive polymer, for example PEDOT:PSS, or a conductive polymer nanofiber, in particular polyaniline nanofiber. A retaining element composed of these materials exhibits an excellent antistatic effect.

The retaining element is nevertheless preferably constructed of polyurethane. Such retaining elements exhibit a favorable compromise between mechanical parameters of elasticity, surface roughness, and pressure resistance, whereby an excellent immobilization of the sample will be achieved with a sufficiently tight bundling (if needed). Elasticity (units for example: elongation in %, ASTM Test D-412) shall be understood to be the deformability of a polymer under tension and pressure loads. Surface roughness shall be understood to be the character of the polymer surface (unit: $\square$m), which relates with the coefficient of friction $\square$ (unit: dimensionless). Generally softer materials exhibit a higher and harder materials a lower coefficient of friction (corresponding to a dry coefficient of friction $\mu$=0.3-0.4 for soft materials (<85° Shore A hardness), and $\mu$=0.15-0.25 for hard materials (>85° Shore A hardness). Pressure resistance (units for example: $Nmm^2$) denotes the resistance of a polymer to the effects of axially applied pressure forces. When the pressure stress exceeds the pressure resistance of the polymer, the polymer tears. These advantageous material properties may be affected by the geometric parameters of the retaining element. Generally for a larger wall thickness, a greater force per unit area $(N/m^2)$ is required for shard-free separation of the segments, which corresponds to pressing apart the working material. In general, the greater the force required for cutting, the greater the load is on the cutting device as well. In particular, retaining elements composed of polyurethane with a wall thickness of approximately 1 mm exhibit the advantageous combination of sufficient elasticity and surface roughness, which prior to cutting make sufficient immobilization and potentially bundling of the sample possible, and after cutting allows rapid separation of the retaining element sections from the sample, and sufficient pressure resistance that largely counteracts a deformation of the retaining element occurring during cutting though squeezing, prevents extrusion of the sample during the cutting procedure, and wears the cutting device as minimally as possible.

In a further preferred implementation, the retaining element is formed out of paper. To reduce its high surface resistance in dry condition (>$10^{14}\square$), this can be provided in a preferred embodiment with an antistatic coating to increase the conductivity. For the antistatic coating, the coatings such as described above can be used. Retaining elements of paper with high material smoothness (measured according to the airflow process according to Bekk, Parker Print Surf, or Bendtsen) offer additional advantageous properties for the separation of the portions of the sample and the retaining element following the cutting procedure.

In a preferred implementation, the retaining element can be moved with the assistance of a controllable and calibratable driving means. In particular, the retaining element can be fastened to a guiding device and moved by means of a controllable driving means. Controllability of the movement is to be understood according to the invention as movement imparted by appropriate control signals in a defined spatial direction in a certain period of time by an amount of length (feed rate) pre-selected by the user. According to the invention, the defined spatial direction is understood to be in a first spatial direction. A preferred drive means may provide an advancement of the sample to be cut by means of the guiding device in stop and go operation, wherein the retaining element and/or a sample can be stopped for cutting, and subsequently advanced by the defined feed rate.

Drive means are known and described in the prior art. In the device according to the invention, the type of drive means is in principle not subject to any restrictions. Ideally, the advancement is performed by a motor or manually; preferably the drive is by motor, in particular electrical. Such a drive means has the advantage that one or especially multiple retaining elements can be moved during the cutting procedure by the pre-selected amount of length in a first spatial direction, wherein a renewed manual setting of the feed rate is possible, but is not required. This is especially advantageous for cutting large amounts of samples, which is desirable for example for the production of hair reference samples. The stop and go operation that is advantageous for the cutting process can be effected by a sensor that detects the user-defined control characteristics, such as the advancement length, and controls the drive means.

The cutting device can make it possible to completely separate the sections from the original sample. A saw or a knife can be used as the cutting device. In particular, a shard-free cutting may occur in the form of a wedge cutting process, wherein one or two blades may be used. Ideally, the cutting device is formed by a fixed knife blade lying in guide rails, which exhibits a front end supporting a cutting edge and a back end. The cutting edge is here selected from a straight, curved, angled, or perforated form. In a preferred implementation, the cutting device is a knife with straight or angled cutting edge, which may be sharpened to be plano-concave, wedge shaped, or in the form of a plane. A plane-shaped sharpening of the knife is especially advantageous. In particular is it advantageous, when only the side of the knife facing the section to be cut away is sharpened, whereas the side of the knife facing the cut sample is formed flat in vertical direction. The leading sharpening angle of approximately 45° can increase the stability of the knife and also make it possible to use for harder material compositions of the retaining element and/or of the sample. The knife is preferably composed of a material that is selected from steel, hard metal, or glass, in particular it is composed of hardened steel.

The cutting device is preferably movable between a first and second position to cut the sample, corresponding to the nature of a falling blade or impact knife (i.e., Guillotine). In a preferred implementation, the cutting device can be moved back and forth between a first position (rest position) and a second position (operational position) with the assistance of a controllable drive means. Preferably the knife exhibits a cutting edge that is arranged substantially perpendicular to the longitudinal axis of the retaining element, both in the first as well as in the second position. Here the spatial orientation of the cutting movement lies substantially perpendicular to the longitudinal axis of the retaining element, wherein the cutting device can approach the retaining element from any direction, preferably a vertical movement will be performed. The retaining element and/or the sample are preferably stabilized for the cutting procedure in a guide opening, wherein the cutting movement will be performed essentially closely adjacent to the guide opening.

In an additional aspect, the present invention relates to a method to cut hair, fibers, or thin, flexible materials. The device according to the invention may be used in the method. Here the method comprises the following consecutive steps. In a first step (Step (A)), the method comprises insertion, alignment, and/or bundling of a sample, comprising a multiplicity of hairs, fibers, or thin, flexible materials, into the cylindrically formed interior of the at least one retaining element. In a second step (Step (B)), the method comprises cutting the sample and the retaining element with the cutting device. Herein a cut specimen will be produced. The cut specimen comprises a section of a multiplicity of segments of hairs, fibers, or thin, flexible materials and a section of the retaining element.

In Step (A), preferably approximately 200 to 800 individual hairs, in particular 375 to 560 individual hairs are simultaneously inserted, aligned, and immobilized, with an average length density of 1 mg/15 cm. For the production of reference hair samples (for example), the individual hairs are preferably folded in the middle prior to insertion, so that only approximately 100 to 400, preferably 190 to 280 individual hairs are used for the filling. Here the respective individual hairs can be cut at least twice in a Step (B) and the section containing the fold can be discarded. For the same original amount of donated hair, the volume percentage of the cut material per retaining element will accordingly be doubled, whereby the homogeneity of the sample is increased due to the bundling. Filling with hair that has been folded in the middle represents accordingly a particular advantage, since the availability of donated hair for the preparation of reference materials is limited.

In a preferred implementation, Step (B) will be performed at least twice consecutively.

In an additional preferred implementation, the method comprises a third step (Step (C)), which is performed after Step (B). Step (C) comprises contamination-free collection of the cut specimen.

In a preferred implementation, the steps (B) and (C) are performed respectively at least twice, alternating consecutively.

In a preferred implementation, the method comprises a fourth step (Step (D)), which is performed after Step (C). Step (D) comprises the separation of the sections of the retaining element from the segments of hairs, fibers, or thin, flexible materials to produce cut particles of a defined length. Here the sections of the retaining element may be retained in a sieve with mesh dimension that is smaller than the cross-section of the retaining element and substantially larger than the cross-section of individual sample components. Simultaneously, the segments of the sample material can be collected through the sieve free of contamination in a collection means.

In a preferred implementation of the present invention, the Steps (B), (C), and (D) are performed in this order at least twice consecutively.

The method according to the invention may be used for production cut specimens, comprising a multiplicity of segments of hairs, fibers, or thin, flexible materials and a section of the retaining element. The multiplicity of segments of hairs, fibers, or thin, flexible materials are detachably immobilized in the section of the retaining element after Step (B) or during Step (C).

In a preferred implementation the cut specimen comprises a length from 0.1 to 5 mm between the cutting surfaces, in particular a length from 0.2 to 4 mm, especially a length from 0.5 to 3 mm Segments of homogeneous length thus generated are particularly advantageous for the production of hair reference materials, since their structural characteristics must approach those of authentic hair as closely as possible for comparability reasons. The preservation of the hair's structural integrity is a particular advantage in comparison to the grinding method for producing hair reference samples known from prior art, because the products from this method have a homogeneous particle size, but the structural differentiation of the hair sections, consisting of cuticle, cortex, and medulla (matrix), is completely destroyed. Especially with the manually cut hair samples commonly used in forensics and toxicology, these reference materials have only minimal comparability.

In a third aspect, the present invention relates to a method to cut hairs, fibers, or thin, flexible materials with the use of the means according to the invention. The method comprises in this aspect the following consecutive steps: In a first step (Step (A)), the method comprises the insertion, alignment and/or bundling of a sample, comprising a multiplicity of hairs, fibers, or thin, flexible materials, in the cylindrically formed interior of the device's at least one retaining element. In a second step (Step (B')), the method comprises the advancement of the sample within the cylindrical interior by use of a plunger. In a third step (Step (C')), the method comprises cutting the sample with the cutting device above the retaining element, to produce a cut specimen comprising a multiplicity of segments of hairs, fibers, or thin, flexible materials. Here the cut specimen contains a multiplicity of segments of hairs, fibers, or thin, flexible materials.

In a fourth aspect, the present invention relates to the use of the device according to the invention, or one of the methods according to the invention, for production of hair particles of a specified length for segmental hair analysis.

In a fifth aspect, the present invention relates to the use of the device according to the invention, or one of the methods according to the invention, for production of reference samples for hair analysis.

In a sixth aspect, the present invention relates to a hair segment of defined length. The hair segment can be produced by use of the device according to the invention, or with the assistance of one of the methods according to the invention.

BRIEF DESCRIPTION OF THE FIGURES

Several particular embodiments of the invention are exemplarily but not exhaustively described as follows, with reference to the attached figures.

The particular embodiments serve only to illustrate the general inventive thought; however, they do not limit the invention.

Figure 1:
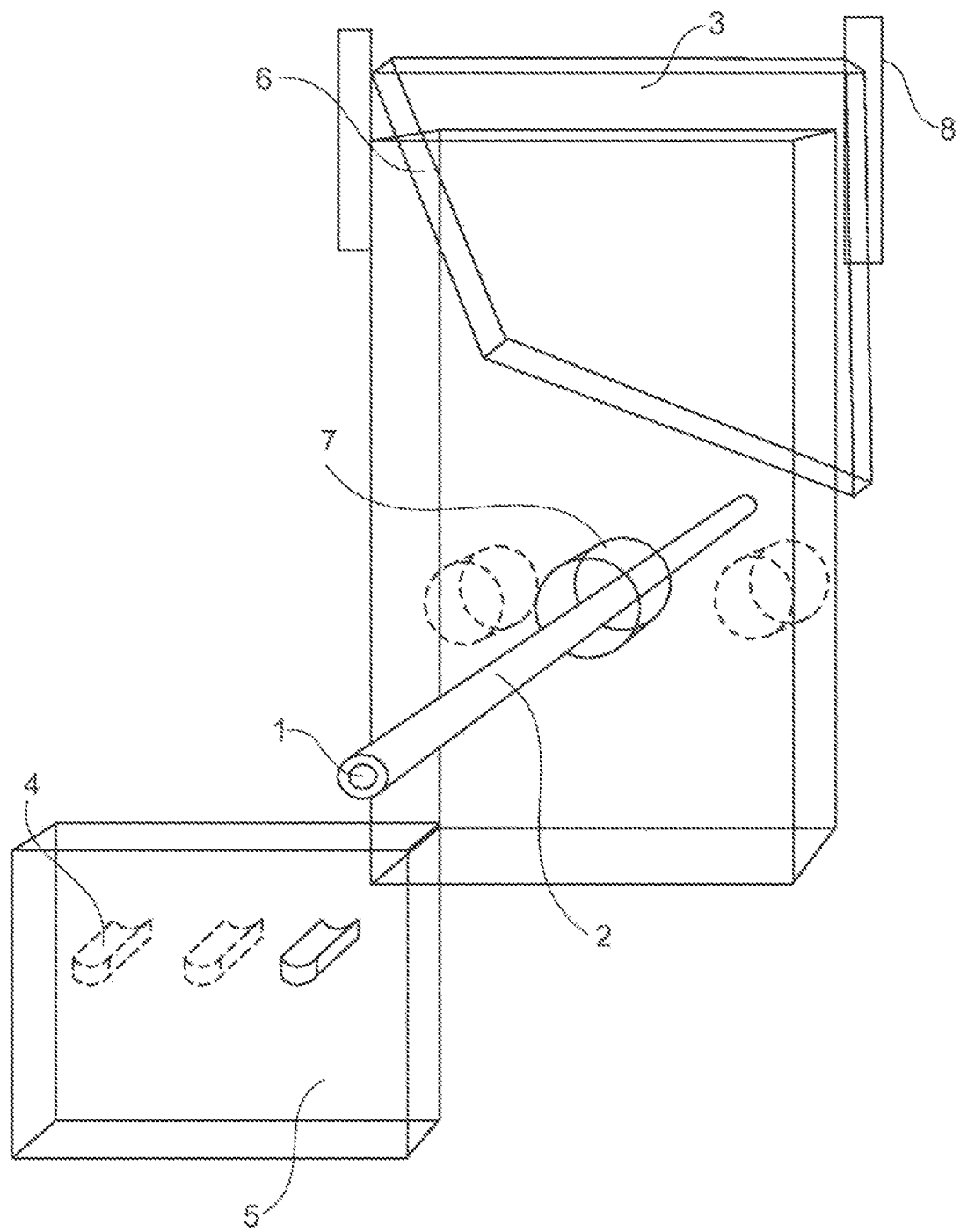

The particular embodiments show:

FIG. 1: A schematic view of the device according to the invention.

Figure 2:
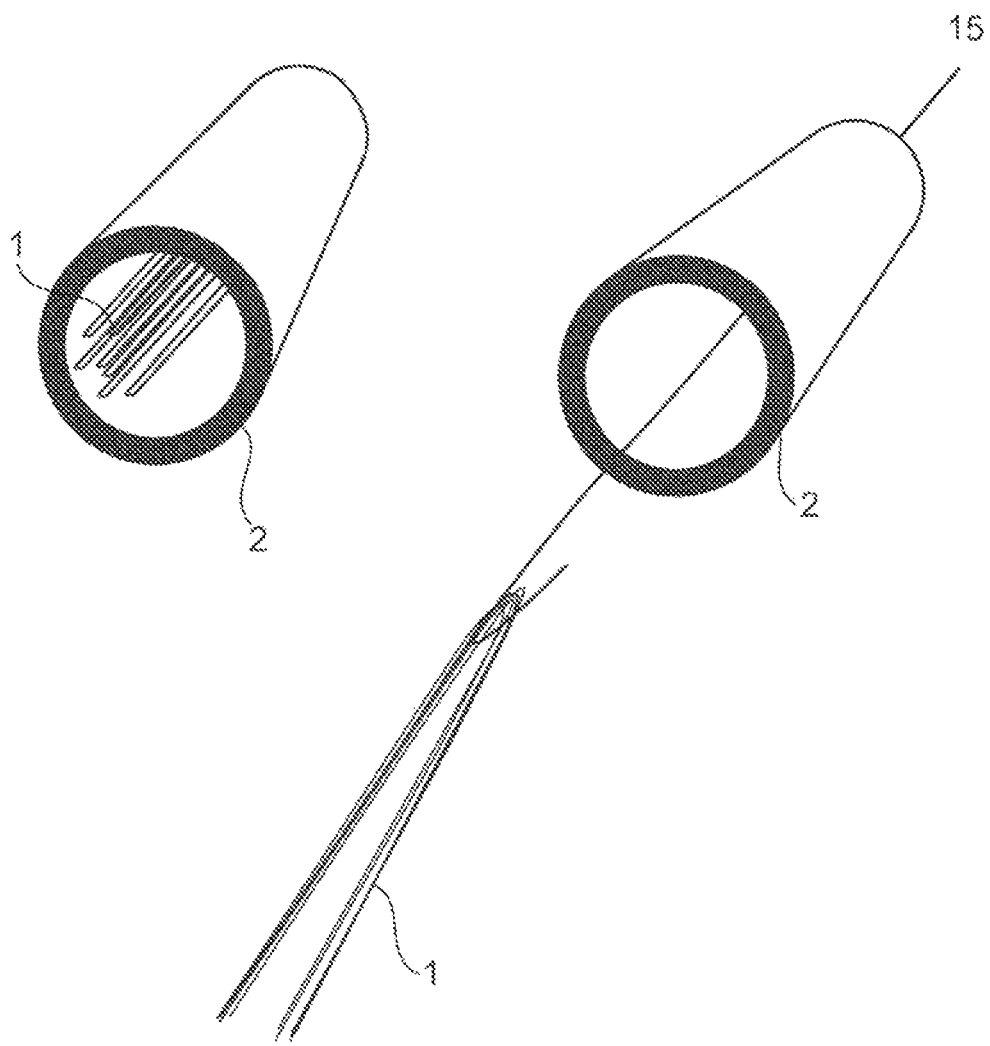

FIG. 2: A detail view of a retaining element (2) in the device according to the invention.

Figure 3:
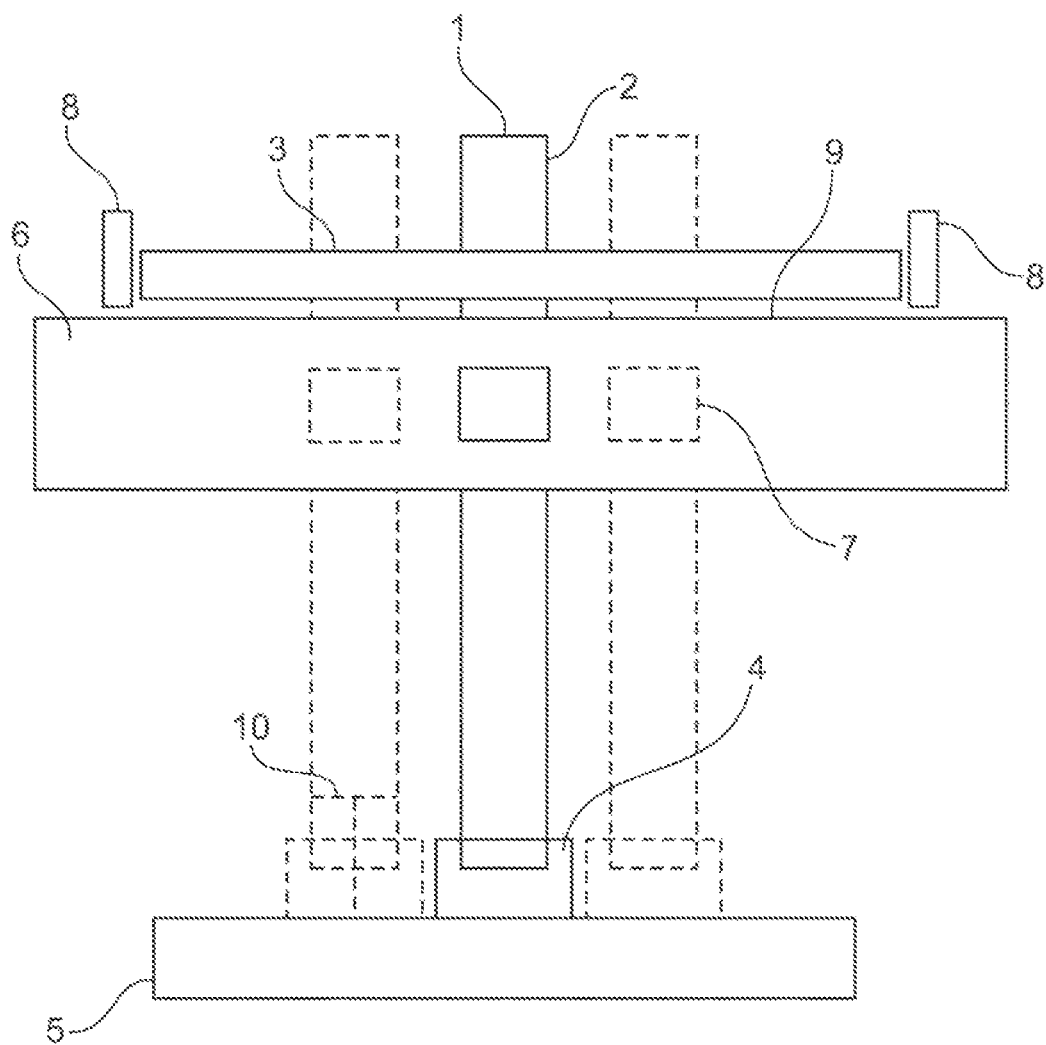

FIG. 3: A top view of an embodiment of the device according to the invention.

Figure 4:
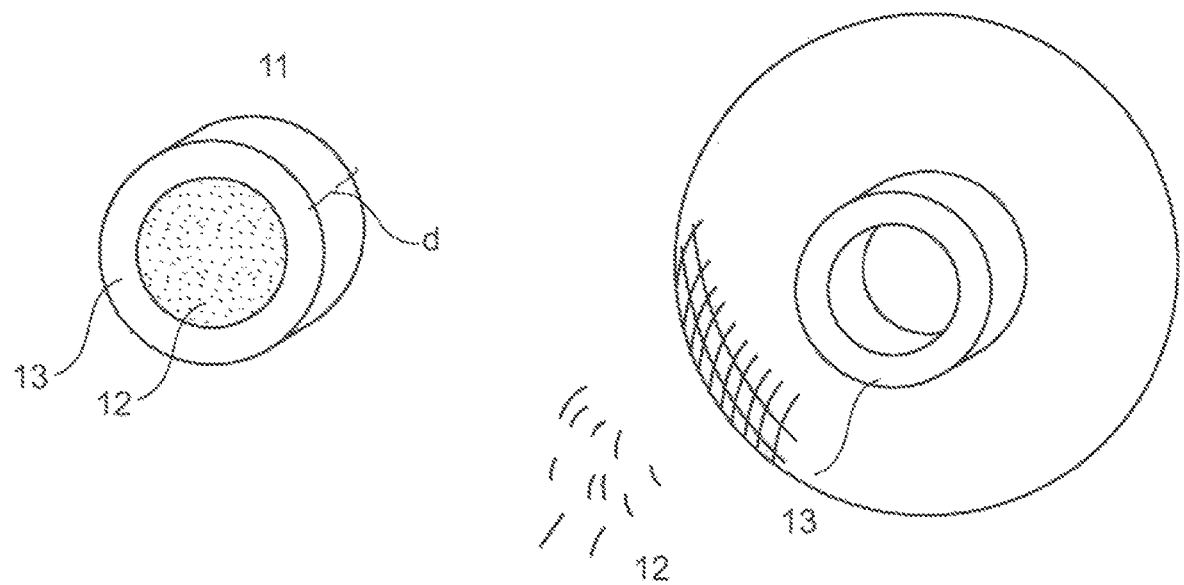
Figure 4:
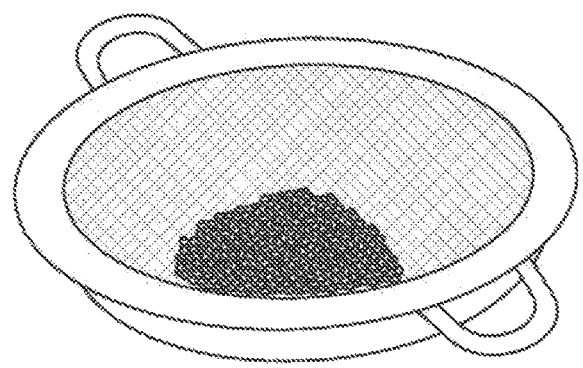
Figure 4:
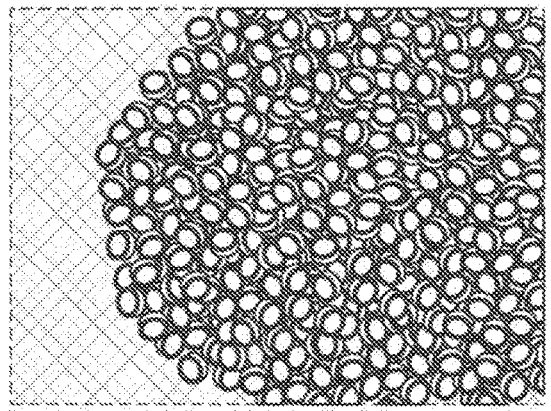

FIG. 4: A top view of cut specimens according to the invention.

Figure 5:
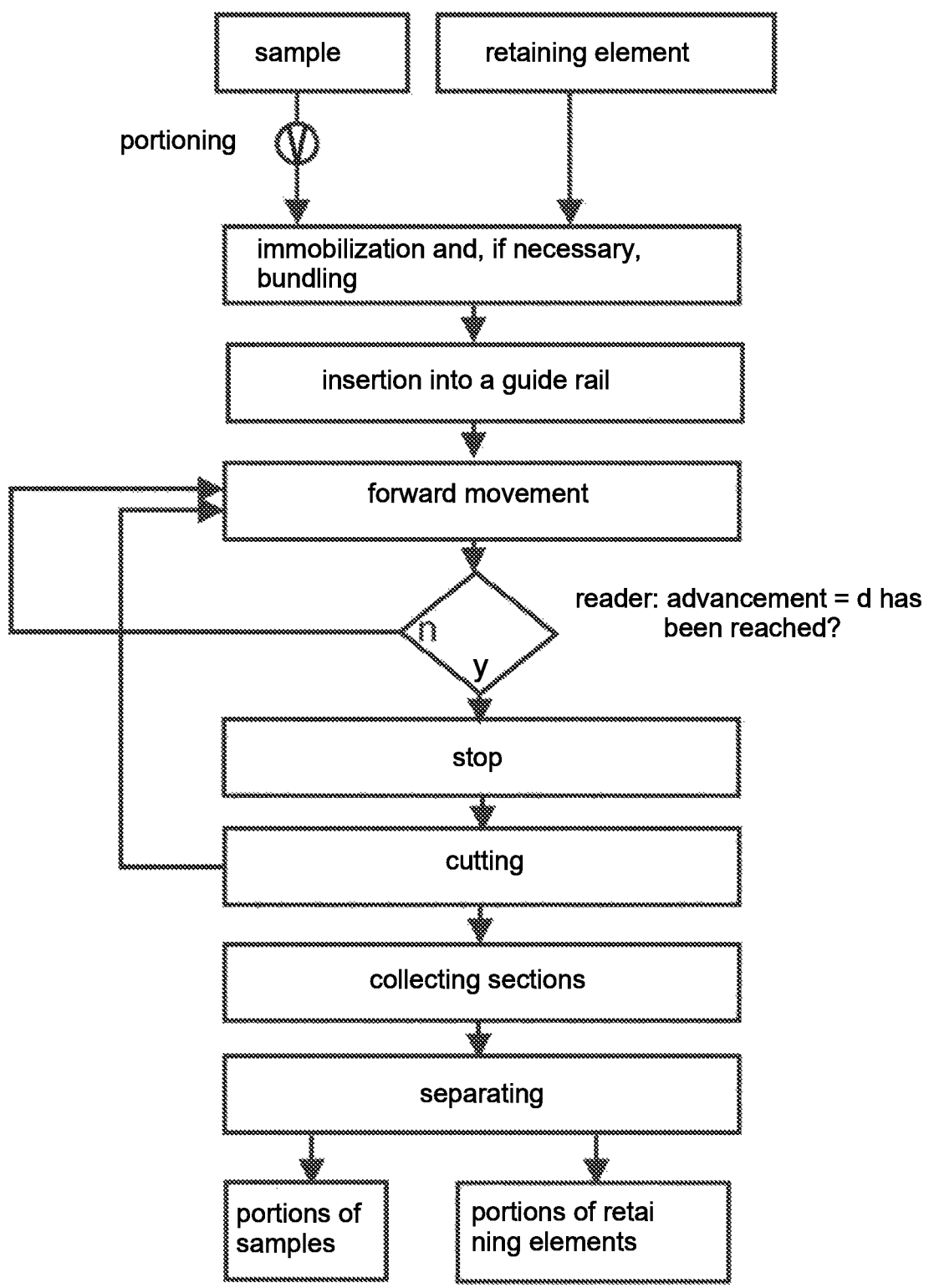

FIG. 5: An embodiment of the method according to the invention as a schematic process diagram.

PREFERRED EMBODIMENTS OF THE INVENTION

FIG. 1 shows a schematic view of an embodiment of the device according to the invention. The device comprises at least one retaining element (2) with a cylindrically formed interior that is suitable to immobilize and potentially to bundle a sample (1) to be cut, which is composed of a multiplicity of hairs, fibers, or thin, flexible materials, in the lengthwise direction of the retaining element (2). The device comprises in addition at least one guide rail (4), which is arranged on a moving element (5), and which is suitable to align the retaining element in at least one guide opening (7) located in a plate (6) standing essentially perpendicular to the retaining element. The device comprises in addition a cutting device (3) that is suitable to cut the fibers or thin, flexible materials bundled and immobilized in the lengthwise direction of the retaining element, substantially perpendicularly to the cylinder axis of the interior of the retaining element (2). The movable plate can be moved with the assistance of a motor in the direction of the cutting device, by an amount defined by the user, i.e., the feed rate (V). Operation of the device occurs in stop & go mode, because it is necessary to cutting at a standstill (V=0) of the retaining element (2) and sample (1) to achieve a sufficiently high cutting accuracy. Stoppage of the retaining element (2) when reaching the advancement value V shall be controlled by a sensor, in this case a light sensor. The sensor is located here in the knife-side portion of the device.

Since any number of retaining elements (2) can be used, the device can be used in this embodiment for the economical production of sufficiently large (=commercially exploitable) batches of reference hair of sufficient homogeneity, so that even small portions of the hair batch, for example, amounts in the range of 50 mg to 100 mg used for toxicological studies, are still sufficiently representative of the composition of the entire batch. Here, the hair material is not destroyed by grinding, as in the alternative method, so that its structural integrity is maintained. These are crucial prerequisites to be able to use such a type of material as a so-called reference material for any sort of hair analyses.

By cutting with assistance of the device, hair segments can be obtained in a controlled size distribution. Individual fractions thus produced from various hair donors can be mixed into homogeneous batches and divided into small portions for use as reference material, without the risk of separative processes that are driven by strong size differences among the individual fractions. The reference material thus produced can for example be used for forensic purposes in measuring methods known from the prior art, for example, such as analysis by gas chromatography-mass spectrometry (GC/MS), tandem gas chromatography/mass spectrometry (GC/MS/MS), or tandem liquid chromatography/mass spectrometry (LC/MS/MS). Due to the high homogeneity of the samples, the analysis results are highly reproducible.

FIG. 2 shows a detail view of a retaining element (2) in the device according to the invention. The sample (1), for example of hair, can be pulled into the retaining element (2), so that the hairs lie tightly bundled with one another. During the insertion, for example by means of an eyelet (15), the hair is advantageously combed, so that a longitudinal slippage of the sample is no longer possible. The retaining element (2) may be a tube or pipe composed of inorganic or organic plastic, metal, paper or wound pipe. Alternatively, the retaining element (2) may also be a sleeve composed of these materials. The retaining element may exhibit any desired form, such as for example a round, flat, or angular form as well.

In this example, the retaining element (2) is a tube cartridge with a length of 8 cm. With the assistance of the tube cartridge, 0.2 g to 0.3 g of hair can be loaded (i.e., immobilized and potentially bundled). At 1 mg weight per 15 cm of hair length (corresponding to the average value for European hair) or a hose, this tube cartridge load corresponds to an amount of 375-560 individual hairs per tube, lying adjacent to one another. Since the hair strands are folded in the middle when pulled into the tube, which results in a doubling of the individual hairs adjacent in the tube, this means that a tube can be filled with approximately 17 to 18 cm long strands of hair, consisting of about 190 to 280 individual hairs. Because of the doubling, the work can be performed especially advantageously and cost effectively with less raw material per hair donor, because immobilization and bundling causes a higher packing density of the doubled hair sample in the retaining element.

In a preferred embodiment, the retaining element comprises an interior diameter of 3 mm and an exterior diameter of 4 mm and is composed of polyurethane (PUR, PU), in particular of transparent material. This makes it possible to see the sample within the holding element from the outside. The material in the retaining element is heat resistant up to approximately 60 or 70° C., and is in addition partially resistant to acid and/or oil. The wall thickness is 0.5 to 1 mm. For example, a tube from the Rexroth company (TU1-8-PUR 4×0.75) can be used as retaining element. Alternatively or simultaneously, the retaining element can be provided with an antistatic-acting inner layer, or can be constructed of antistatic-acting plastic, to counteract electric charging of the sample and retaining element occurring during the cutting procedure. In order to obtain segments largely free from contamination, plastic tubes with permanent antistatic properties can be used.

FIG. 3 shows a top view of an embodiment the device according to the invention. Two additional retaining elements are shown by dotted lines, wherein the number of retaining elements is fundamentally not subject to restriction. The device is suitable for cutting hair for forensic and toxicological purposes. Within the device, the hairs are separated together with the retaining material by a cutting device (3), consisting of a knife, a saw, or a grinding disk, at a length of 0.2 to 4 mm, in particular a length of 0.5 to 3 mm. A knife lying in guide rails (8) is preferably used, which can be located in a rest position and an operating position. In a preferred embodiment, the guide rails are movable in horizontal direction parallel to the plate and can be set, wherein the position of the cutting device relative to the position of the guide openings (7) can be adjusted, whose number is also fundamentally not limited. The cutting edge of the blade, which is mechanically loaded to various degrees depending on position in the process of cutting, can thus be moved, wherein the wear is distributed evenly over the entire cutting edge, and thus the operational life of the blade can be extended and its holding time may be reduced. The cutting movement takes place substantially perpendicular and vertically toward the axis of the interior of the holding element. In this example, the knife is honed in the shape of a plane, with an angled knife blade, and its planar side is located at a specified separation distance (9) d from the plate (6), which possesses guide openings (7). The separation distance (9) d is here at most 1 mm. The angled construction of the blade's cutting edge serves in addition to make a pulling movement possible during the essentially vertically directed cutting movement (in the manner of a guillotine), thus resulting in a lower mechanical load on the knife's cutting edge and a smoother cut edge in the cut section.

In another example, the hair is pushed with a plunger (10) out of a pipe serving as retaining element and is cut in front of the pipe.

FIG. 4 shows a top view of multiple specimens (11) cut according to the invention. The cut specimens consist in this case of tube rings and cut hair, which can be separated by subsequent processing, for example by sieving, into individual components, the portions of the sample (12) and of the retaining element (13). The elasticity of a retaining element formed from polymer significant influence the separability of sample and retaining element, in particular sections with relatively low elasticity permit quick and largely contaminant-free separation of the portions ("falling out"). The thoroughness of the separation of the portions of the retaining element and sample is promoted by a minimal retention of sample on the retaining element. The retention can be reduced by the holding element's anti-static properties, and by a minimal surface roughness.

FIG. 5 describes a potential embodiment of the method schematically, using an individual retaining element filled with the sample. Here, a sample (1) of a multiplicity of hairs, fibers or other thin, flexible materials is portioned and immobilized and potentially bundled in a retaining element (2). After insertion into a guide rail (4), the retaining element is moved by means of a movable plate (5) in the direction of a fixed plate (6), which is provided with a guide opening (7). The movement through the guide opening occurs at the feed rate V selected by the user. The advancement occurs in this embodiment by motor, and can be controlled by means of a sensor arranged on the knife side, for example, a light sensor. When the set advancement is achieved, the movable plate (5) comes to a standstill, corresponding to the stop-and-go operation of the device, and the cutting device (3) performs a cutting operation. The section (11) consisting of sample (1) and retaining element (2) is collected in a suitable device, for example a sieve (step C). The corresponding portions of the sample (12) and the retaining element (13) can subsequently be separated by a suitable process, for example by a mechanical separation process (step D).

LIST OF REFERENCE NUMBERS

1 Sample of hair, fiber, or other thin, flexible material
2 Retaining element
3 Cutting device
4 Guide rail for the retaining element
5 Movable plate
6 Fixed plate
7 Guide opening
8 Movable guide rail for cutting device
9 Separation distance d
10 Plunger
11 Section
12 Section of the sample, composed of multiple cut segments of hair
13 Section of the retaining element
14 Fixed end of the sample
15 Eyelet

I claim:
1. A method for producing a sample of hair, comprising:
   a) providing a device comprising:
      i) a plate having a top end and a lower end, wherein said plate is a single continuous body comprising a plurality of openings each configured to receive an elongated tubular retaining element containing a sample of hair, wherein said plate is not configured to clamp said elongated tubular retaining element while said elongated tubular retaining element occupies said openings;
      ii) a guiding element arranged parallel to said plate and comprising a plurality of guiding element guide rails arranged perpendicularly to said guiding element wherein said guiding element guide rails are configured to align said elongated tubular retaining element perpendicular to said plate when said elongated tubular retaining element is inserted through said openings; and
      iii) a cutting element configured to cut said elongated tubular retaining element while said retaining element occupies said openings, wherein said cutting element is arranged parallel to said plate with said cutting element being held parallel to said plate by a pair of cutting element guide rails connected to said plate wherein said pair of cutting element guide rails are configured to guide said cutting element from said top end towards said lower end of said plate;
      iv) wherein said plurality of openings and said plurality of guiding element guide rails are equal in number and are collinear with one another;
   b) inserting a sample of hair into at least one linear elongated tubular retaining element;
   c) inserting said at least one elongated tubular retaining element containing said sample into said openings in said plate; and
   d) activating said cutting element to cut said at least one elongated tubular element containing said sample to produce a sample unit comprising a segment of said at least one elongated tubular retaining element and a portion of said sample.

2. The method of claim 1, further comprising repeating said activating step to produce a plurality of sample units from said at least one at least one elongated tubular retaining element containing said sample.

3. The method of claim 2, wherein said plurality of sample units are uniform in length.

4. The method of claim 1, further comprising collecting said sample unit under contamination free conditions.

5. The method of claim 1, further comprising separating said segment of said elongated tubular retaining element from said portion of said sample.

6. The method of claim 5, further comprising subjecting said portion of said sample to chemical analysis.

7. The method of claim 1, wherein said portion of said sample is subjected to chemical analysis.

8. The method of claim 1, wherein said portion of said sample is subjected to segmental hair analysis.

9. A sample unit produced according to the method of claim 1.

* * * * *